United States Patent [19]
Gormley et al.

[11] Patent Number: 5,853,700
[45] Date of Patent: Dec. 29, 1998

[54] HYDRO-ALCOHOLIC AEROSOL HAIR COSMETIC COMPOSITIONS CONTAINING A HYDROLYTICALLY STABLE SILICONE GLYCOL BLOCK COPOLYMER DISPERSION

[75] Inventors: John L. Gormley, Midland Park; Gary T. Martino, Plainsboro, both of N.J.

[73] Assignee: National Starch and Chemical Investment Holding Corporation, Wilmington, Del.

[21] Appl. No.: 744,294

[22] Filed: Nov. 6, 1996

[51] Int. Cl.$^6$ ........................................ A61K 7/11
[52] U.S. Cl. ................. 424/47; 424/45; 424/DIG. 1; 424/DIG. 2; 424/70.11; 424/70.1; 132/202
[58] Field of Search .................. 424/45, 47, DIG. 1, 424/DIG. 2, 70.11, 70.1; 132/202

[56] References Cited

U.S. PATENT DOCUMENTS

| | | | |
|---|---|---|---|
| 4,543,249 | 9/1985 | Nelson | 424/70.11 |
| 4,871,529 | 10/1989 | Sramek | 424/47 |
| 4,906,459 | 3/1990 | Cobb et al. | 424/70.11 |
| 4,983,418 | 1/1991 | Murphy et al. | 424/47 |
| 5,176,898 | 1/1993 | Goldberg et al. | 424/47 |
| 5,286,477 | 2/1994 | Bhatt et al. | 424/47 |
| 5,292,847 | 3/1994 | O'Lenick, Jr. | 528/14 |
| 5,314,684 | 5/1994 | Horoschak et al. | 424/70.11 |

FOREIGN PATENT DOCUMENTS

| | | |
|---|---|---|
| 0 260 641 | 3/1988 | European Pat. Off. . |
| 38 42 765 | 12/1988 | Germany . |
| 5-347849 | 12/1993 | Japan . |
| 1 424 002 | 5/1972 | United Kingdom . |

*Primary Examiner*—Raj Bawa
*Attorney, Agent, or Firm*—Karen G. Kaiser

[57] ABSTRACT

A low volatile organic compound hair cosmetic composition containing a water insoluble, hydrolytically stable polypropylene oxide-modified polydimethylsiloxane block copolymer exhibits excellent spray characteristics and minimized contact foaming while providing high curl retention, fast drying time and low initial curl droop. The composition contains 0.001 to 0.9% of a polypropylene oxide-modified polydimethylsiloxane block copolymer which contains essentially no ethylene oxide, 1 to 15% of a film-forming resin, up to 70% of a solvent, 10 to 60% of a propellant, and water.

17 Claims, No Drawings

HYDRO-ALCOHOLIC AEROSOL HAIR COSMETIC COMPOSITIONS CONTAINING A HYDROLYTICALLY STABLE SILICONE GLYCOL BLOCK COPOLYMER DISPERSION

BACKGROUND OF THE INVENTION

The present invention relates to hair cosmetics, particularly hair fixative compositions, containing no more than 80% volatile organic compounds and a polypropylene oxide-modified polydimethylsiloxane block copolymer additive.

In their most basic form, hair cosmetic compositions contain a film-forming polymer, which acts as the cosmetic, and a delivery system, which is usually one or more alcohols or a mixture of alcohol and water. In the case of aerosol delivery, the delivery system will also contain a propellant, typically a volatile hydrocarbon. Due to environmental regulations controlling the emission of volatile organic compounds (VOCS) into the atmosphere, VOC emissions have been restricted to 80% in some states, and may be restricted to 55%, by weight of the hair cosmetic formulation. As used herein, a volatile organic compound is an organic compound containing from 1 to 10 carbon atoms, which has a vapor pressure of at least 0.1 mm Hg at 20° C. and is photochemically reactive. Water is generally substituted for at least a portion of the volatile organic compounds and so has become a greater component in hair cosmetic compositions. Unfortunately, many cosmetic polymers currently used in hair cosmetic compositions exhibit a loss of spray performance properties in aqueous based systems. Many of the standard resins, when delivered in a low VOC aerosol system, foam at the actuator valve and on the hair. Foaming is generally considered to be a function of viscosity, surface tension, and the surface activity of the hair cosmetic polymers in solution. These factors have prompted the search for additives to improve the spray characteristics of hair cosmetic compositions that contain 80% or less VOCs, hereinafter referred to as low VOC.

Several low VOC hair cosmetic compositions are known in the art. For example, U.S. Pat. No. 5,286,477 discloses an aqueous hair spray composition which contains a terpolymer of vinylpyrrolidone/ethyl methacrylate/methacrylic acid and, in a preferred embodiment, polydimethylsiloxanes.

However, low VOC hair cosmetic compositions have the disadvantage of poor spray characteristics resulting from various phenomenon such as elongational viscosity, surface tension, large particle size, and foaming. The use of spray enhancers, such as cyclic and other low molecular weight silicones has been reported to give aesthetically pleasing sprays in low VOC hair cosmetic compositions. For example, U.S. Pat. No. 5,176,898 discloses an aqueous hair spray containing a volatile silicone.

Unfortunately, the use of such enhancers do not reduce contact foaming and may even increase the stability of such foams. Contact foaming, as used herein, refers to foaming on the hair.

The use of dimethicone copolymers, particularly polyalkylene oxide-modified polydimethylsiloxane block copolymers, in hair cosmetic compositions is known in the art. Traditionally, these additives offer conditioning properties such as gloss and improved combing due to reduced stiffness. Low VOC hair cosmetic compositions known in the art which contain polyalkylene oxide-modified polydimethylsiloxane block copolymers include: U.S. Pat. No. 4,871,529 which discloses a hair spray composition containing a silicone copolymer such as polyethylene oxide-modified polydimethyl siloxane block copolymers or a combination of polyethylene- and polypropylene-oxide-modified polydimethyl siloxane block copolymers; DE 38 42 765 A1 which discloses hair sprays which contain a combination of trimethylalkylammonium chloride, a quarternized hydroxyalkyl cellulose polymer, and a polyorganosiloxane-polyoxyalkylene copolymer; and EP 260 641 which discloses an emulsion hair cosmetic containing a dimethylpolysiloxane polyoxyalkylene copolymer, including a combination of polyethylene- and polypropylene-oxide-modified polydimethyl siloxane block copolymers.

All of the literature disclosing polyalkylene oxide-modified polydimethylsiloxane block copolymers use either polyethylene oxide or a combination of polyethylene oxide and polypropylene oxide. None of these patents discloses the use of a polypropylene oxide-modified polydimethylsiloxane block copolymer alone. JP5 347849 discloses hair compositions containing polyoxyalkylene modified silicones, including polypropylene oxide-modified polydimethylsiloxane block copolymers. However, it never states that the polypropylene-modified copolymers may be used alone. The patent application discloses hair compositions containing polyoxyalkylene modified silicones, amphoteric polymers, and a starch syrup which provides excellent setting ability, is free from stickiness, and provides the hair with a sheen and a natural, supple feeling. The patent application concentrates on hair lotions and other non-aerosol hair compositions.

Further, JP5 347849 states that the starch syrup is an essential ingredient for such a composition. Starch syrup, as defined in this patent application, is obtained by hydrolyzing starch with a weak acid or an enzyme. As used in the industry, a starch syrup is an aqueous solution of nutritive saccharides with a dextrose equivalent (DE) of at least 20. DE is defined as the reducing power of the hydrolysate. As each starch molecule has one reducing end, DE is inversely related to molecular weight. The DE of anhydrous D-glucose is defined as 100 and the DE of unhydrolyzed starch is virtually zero.

Surprisingly, it has now been discovered that a low VOC aerosol hair cosmetic composition containing a water insoluble, hydrolytically stable polypropylene-modified polydimethylsiloxane block copolymer, but without a starch syrup, provides high curl retention, fast drying time, low initial curl droop, excellent spray characteristics including small particle size and good spray distribution, and improved minimization of contact foaming.

SUMMARY OF THE INVENTION

The present invention is directed to a low VOC hair cosmetic composition, particularly hair fixative compositions, giving improved spray characteristics, particularly minimized contact foaming, while providing high curl retention, fast drying time, low initial curl droop and excellent spray characteristics, including small particle size and good spray distribution, by the inclusion of a polypropylene oxide-modified polydimethylsiloxane block copolymer, particularly one which is water insoluble and hydrolytically stable.

The instant hair cosmetic composition contains by weight from about 0.001 to about 0.9% of a polypropylene-oxide-modified polydimethylsiloxane block copolymer, particularly one which is water insoluble and hydrolytically stable, from about 1 to about 15% of a film-forming resin, from about 10 to about 60% of a propellant, from zero to about 70% of a solvent such as a lower alcohol, and sufficient water to bring the composition up to 100%.

The instant invention is further directed to a method for improving the spray characteristics and decreasing the contact foaming of a hair cosmetic composition by addition of from about 0.001 to about 0.9% by weight of a polypropylene oxide-modified polydimethylsiloxane block copolymer, particularly one which is water insoluble and hydrolytically stable.

An object of the present invention is to provide a hair cosmetic composition containing a polypropylene oxide-modified polydimethylsiloxane block copolymer.

Another object of the present invention is to provide a hair cosmetic composition containing a water insoluble, hydrolytically stable polypropylene oxide-modified polydimethylsiloxane block copolymer.

Still another object of the present invention is to provide a hair cosmetic composition containing a polypropylene oxide-modified polydimethylsiloxane block copolymer which has improved spray characteristics, particularly small particle size and good spray distribution, and minimization of contact foaming.

Yet another object of the present invention is to provide hair cosmetic composition containing a polypropylene oxide-modified polydimethylsiloxane block copolymer which has improved spray characteristics, particularly small particle size and good spray distribution, and minimized contact foaming yet still provides high curl retention, fast drying time, and low initial curl droop.

These and other objects of the present invention will become apparent to one skilled in the art from the following detailed description and examples below.

DETAILED DESCRIPTION OF THE INVENTION

The present invention is directed to a low VOC aerosol hair cosmetic composition, particularly a hair fixative composition, which gives improved spray characteristics, particularly small particle size and good spray distribution, and minimization of contact foaming, yet provides high curl retention, fast drying time and low initial curl droop. This is achieved by the inclusion of a polypropylene oxide-modified polydimethylsiloxane block copolymer, particularly a water insoluble, hydrolytically stable polypropylene oxide-modified polydimethylsiloxane block copolymer.

While polyalkylene oxide-modified polydimethylsiloxane block copolymers have been used in hair cosmetic compositions to add gloss and decrease stiffness, contact foaming has not been eliminated by the addition of such copolymers containing polyethylene oxide. Therefore, it was unexpected to discover that polypropylene oxide-modified polydimethylsiloxane block copolymers when used alone (without polyethylene oxide-modified copolymers), particularly those which are water insoluble and hydrolytically stable, substantially eliminated contact foaming.

The hair cosmetic composition of the instant invention contains by weight from about 0.001 to about 0.9%, particularly from about 0.005 to about 0.4%, of a polypropylene oxide-modified polydimethylsiloxane block copolymer, from about 1 to about 15%, particularly from about 2 to about 10%, of a film-forming resin, from zero to about 70%, particularly from about 10 to about 40% of a solvent such as a lower alcohol, from about 10 to about 60%, particularly from about 20 to about 45% of a propellant, and sufficient water to bring the composition up to 100%.

The hair cosmetic resins whose spray characteristics can be improved include most of the standard polymers known and used in the art. These resins, which can be used individually or in blends, include, but are not limited to, vinyl acetate/crotonates/vinyl neodecanoate copolymer, octylacrylamide/acrylates/butylaminoethyl methacrylate copolymer, vinyl acetate/crotonates, polyvinylpyrrolidone (PVP), polyvinylpyrrolidone/vinyl acetate copolymer, PVP acrylates copolymer, homopolymers of N-vinyl formamide and interpolymers prepared from N-vinyl formamide and at least one vinyl monomer including but not limited to those disclosed by U.S. Pat. No. 5,478,553 (incorporated herein by reference), vinyl acetate/crotonic acid/vinyl propionate, acrylates/acrylamide, acrylates/octylacrylamide, and alkyl esters of polyvinylmethylether/maleic anhydride, diglycol/cyclohexanedimethanol/iso-phthalates/sulfoisophthalates copolymer, vinyl acetate/butyl maleate and isobornyl acrylate copolymer, vinylcaprolactam/ PVP/dimethylaminoethyl methacrylate, vinyl acetate/alkylmaleate half ester/N-substituted acrylamide terpolymers, vinylcaprolactam/vinyl-pyrrolidone/methacryloamidopropyl trimethylammonium chloride terpolymer, methacrylates/acrylates copolymer/amine salt, acrylate polymers, and betain polymers such as N-methacryloyl oxyethyl N,N-dimethyl ammonium-α-N-methyl carboxy betain/alkyl methacrylate copolymer, N-methacryloyl ethyl N,N-dimethyl ammonium-α-methyl carboxy betain homopolymer, methacryloyl ethyl dimethyl betain/methacryloyl ethyl trimethyl ammonium chloride/methoxy glycol methacrylate copolymer, N-methacryloyl ethyl N,N-dimethyl ammonium-α-methyl carboxy betain/N-methacryloyl ethyl-N,N,N-trimethyl ammonium chloride, 2-hydroxy ethyl methacrylate copolymer, and N-methacryloyl ethyl N,N-dimethyl ammonium-α-methyl carboxy betain, N-methacryloyl ethyl-N,N,N-trimethyl ammonium chloride, methoxy polyethylene glycol methacrylate copolymer.

Also encompassed are acrylic polymer resins containing carboxylic acid groups which include without limitation the copolymers of n-tert-octylacrylamide, methyl and/or ethyl methacrylate, hydroxypropyl methacrylate, acrylic acid and t-butyl aminoethyl methacrylate, available from National Starch and Chemical Company under the AMPHOMER® trade name; copolymers of n-tert-octylacrylamide, methyl methacrylate, acrylic acid and t-butyl aminoethyl methacrylate, available from National Starch and Chemical Company under the LOVOCRYL™ trade name; copolymers of vinyl acetate, crotonic acid and a vinyl ester of an alpha-branched saturated aliphatic monocarboxylic acid containing from 5 to 10 carbon atoms in the carboxylic acid moiety, available from National Starch and Chemical Company under the RESYN® trade name; copolymers prepared from unsaturated carboxylic acids containing 3 to 5 carbons, saturated alkyl (particularly those containing 1–6 carbon atoms) esters of acrylic or methacrylic acid, and saturated alkyl (particularly those containing 3–12 carbon atoms) N-substituted acrylamide, available from National Starch and Chemical Company under the VERSATYL® tradename; and copolymers of methylmethacrylate, butyl acrylate, and methacrylic acid, available from National Starch and Chemical Company under the BALANCE™ trade name. Particularly suitable resins are the AMPHOMER and BALANCE resins.

In formulation, some of these polymers require neutralization with an alkaline reagent to effect solubility or dispersibility into the aqueous delivery system and subsequently, after application to the hair, to effect removability with water or with shampoo and water. The amount of base used for neutralization is dependent on the carboxylic acid content and hydrophobicity of the hair cosmetic polymer. The levels of neutralization typically will range from 5 to 100%, depending on the acidity and hydrophobicity of the polymer. Suitable bases for neutralization of the polymer are the standard cosmetically acceptable bases known and used in the art. The preferred bases are sodium hydroxide, 2-amino-2-methyl-1,3-propanediol, dimethyl stearamine, potassium hydroxide, 2-amino-2-methyl-1-propanol, histidine, tris(hydroxymethyl)aminomethane, and triisopropylamine, diethylpropylamine, dimethyl hydrogenated tallow amine, triethanolamine. The choice of the base and the degree of neutralization also affect the flexibility of the resultant hair cosmetic when sprayed on the hair, giving a soft or a hard hold. The choice of which base to utilize and the degree of neutralization required to achieve flexibility is within the expertise of one skilled in the art. In general, however, the amount of base for neutralization will be within the range of 0.05 to 5% based on the total weight of the composition, although it will be recognized that individual formulations may require neutralization outside this range.

The delivery system in most cases will be a blend of water and one or more volatile organic compounds acting as solvents. The total amount of volatile organic compound (VOC) content will be limited by environmental regulations, which in some cases is now mandated at 80% or less, and may soon be at 55% or less, based on the weight of the composition. Typically, the organic solvent will be a lower alcohol (herein defined as an alcohol having from 1 to 7 carbon atoms), particularly methanol, ethanol, propanol, isopropanol, or butanol. Also suitable are acetals and ketones, particularly dimethoxyethane and acetone.

Propellants useful in the instant invention include, but are not limited to, ethers, such as dimethyl ether; one or more lower boiling hydrocarbons such as $C_2$–$C_6$ straight and branched chain hydrocarbons, for example, ethane, propane, butane, and isobutane; halogenated hydrocarbons, such as, hydrofluorocarbons, for example, 1,1-difluoroethane and 1,1,1,2-tetrafluoroethane, present as a liquified gas; and the compressed gases, for example, nitrogen, air and carbon dioxide. The amount of propellant used in the hair cosmetic compositions of this invention may vary from about 10 to about 60%, particularly from about 20 to about 45% by weight of the hair cosmetic composition. It should be noted that most of the above propellants are volatile organic compounds. However, the emission of halogenated hydrocarbons such as hydrofluorocarbons, and the compressed gases are not at this time subject to environmental regulations as they are not photochemically reactive; therefore, these compounds may be formulated into the hair sprays of this invention without inclusion in the total VOC content.

The polypropylene oxide-modified polydimethylsiloxane block copolymer additive is preferably a water insoluble one. Thus, it is generally present in the composition as a colloidal dispersion and is insoluble in hot water. As such, it has no measurable cloud point in water.

The polypropylene oxide-modified polydimethylsiloxane block copolymer is also preferably a hydrolytically stable one. The structure of the propyleneoxy end blocked copolymer significantly affects its hydrolytic stability. The polypropylene oxide groups may be attached at the ends of the silicone backbone through Si—C or Si—O—C bonds. The Si—O—C linkage offers limited resistance to hydrolysis, particularly above a pH of 8. Hydrolysis at alkaline pH occurs so quickly as to offer little if any performance benefit at low use levels. Thus, the hydrolytic instability renders such Si—O—C linked polypropylene oxide-modified polydimethysiloxane block copolymers commercially unsuitable for the instant hair cosmetic compositions.

The Si—C linked polypropylene oxide-modified block copolymers may be of two structural types, the alkoxy-end blocked (AEB) type and the alkyl-pendant (AP) type. Both types are suitable for the instant invention.

The AP type dimethicone copolymers are of the general formula I:

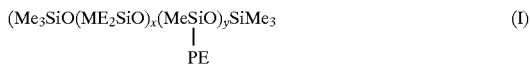

$$(Me_3SiO(ME_2SiO)_x(MeSiO)_ySiMe_3 \quad | \quad PE) \tag{I}$$

wherein PE represents $CH_2CH_2CH_2O\ (PO)_nZ$, and Z represents either hydrogen or a lower alkyl radical, lower alkyl being defined as $C_1$–$C_7$. Such AP type dimethicone copolymers include, but are not limited to Silwet L-7500 (commercially available from OSi Specialties, Endicott, N.Y.). Silwet L-7500 contains about 21% propylene oxide and about 79% silicone by weight.

The AEB type dimethicone copolymers are of the general formula II:

$$PE(Me_2Si)(OSiMe_2)_xPE \tag{II}$$

wherein PE represents $CH_2CH_2CH_2O\ (PO)_nZ$, and Z represents either hydrogen or a lower alkyl radical, lower alkyl being defined as $C_1$–$C_7$. Such AEB type dimethicone copolymers include, Silsoft 900 (commercially available from OSi Specialties, Endicott, N.Y.). Silsoft 900 contains about 25% propylene oxide and about 75% silicone by weight.

Although not needed for spray performance, optional conventional additives may also be incorporated into the hair spray compositions of this invention to provide certain modifying properties to the composition. Included among these additives are plasticizers, such as glycerine, glycol and phthalate esters; emollients, lubricants and penetrants, such as lanolin compounds; fragrances and perfumes; UV absorbers; dyes and other colorants; thickeners; anticorrosion agents; detackifying agents; combing aids and conditioning agents; antistatic agents; neutralizers; glossifiers; preservatives; emulsifiers; surfactants such as dioctylsulfosuccinate; viscosity modifiers; gelling agents; opacifiers; stabilizers; sequestering agents; chelating agents; pearling agents; and clarifying agents. Such additives are commonly used in hair cosmetic compositions known heretofore. These additives are present in small, effective amounts to accomplish their function, and generally will comprise from about 0.1 to 10% by weight each, and from about 0.1 to 20% by weight total, based on the weight of the composition.

To prepare the hair cosmetic composition, a solution of the resin in the water or water/solvent mixture is prepared. Then any optional additives may be added. The mixture is then pressurized with propellant according to conventional standards known in the art to form the aerosol hair cosmetic composition.

When the resin is an acrylic polymer containing carboxylic acid groups and neutralization is desired, the neutralization agent may be added to the non-volatile solvents, such as water or alcohol. The resin is then added with stirring. In certain embodiments, the polymer slurry is heated to a temperature and for a time to form an aqueous, essentially homogeneous solution. Depending upon the resin used, the degree of neutralization, and the solvent system used, the temperature to which the slurry is heated may range from about 60° C. to about 80° C. and the time period over which the temperature is maintained may range from about five minutes to about three hours. The solvent and any optional additives are then added and optionally filtered. The mixture is finally pressurized with propellant according to conventional standards to form the hair cosmetic composition.

Pressures utilized are those conventionally used to prepare aerosol sprays, such as from about 35 psi to about 110 psi.

Hair cosmetic compositions include, but are not limited to, hair fixative compositions and styling aids.

The following examples are presented to further illustrate and explain the present invention and should not be taken as limiting in any regard.

EXAMPLES

The following examples are presented to further illustrate and explain the present invention and should not be taken as limiting in any regard.

Example 1
Preparation of Low VOC Hair Cosmetic Compositions

55% VOC compositions are prepared using the following formulation:

| Ingredient | Parts |
|---|---|
| Balance ™ 0/55 | 9.73 |
| AMP Regular ® | 0.73 |
| Deionized water | Q.S. to 100 |
| Additive | 0.3 |
| Ethanol | 22.0 |
| Dimethyl ether | 33.0 |

The water, ethanol, and AMP are combined. The polymer emulsion, Balance 0/55 is then added, stirring until completely dissolved. The additive is next mixed in. The composition is filtered and filled into aerosol containers which are then charged with dimethyl ether propellant using techniques well known in the art.

Note: Balance™ 0/55 is a 51.4% solid resin acrylate copolymer commercially available from National Starch and Chemical Company.

AMP Regular is 2-amino-2-methyl-1-propanol commercially available from Angus Chemical Co.

The following additives are used:

| Additive | Type | Ratio EO/PO |
|---|---|---|
| Silwet L-722 | AP | 50/50 |
| Silwet L-720 | AEB | All PO |
| Silwet L-7001 | AP | 40/60 |
| Silwet 7002 | AP | 50/50 |
| Silwet L-7200 | AP | 75/25 |
| Silwet L-7500 | AP | All PO |
| Silwet L-7600 | AP | All EO |
| Silwet L-7604 | AP | All EO |
| Silwet L-7605 | AP | All EO |
| Silwet L-7622 | AP | All EO |
| Silwet L-7602 | AP | All EO |
| Silwet L-7087 | AP | 40/60 |
| Silwet L-7657 | AP | All EO |
| Silsoft 900 | AEB | All PO |
| DC-344 | Cyclic | No EO; No PO |

DC-344 is commercially available from Dow Corning Corporation, Midland, Mich.

The Silwet and Silsoft additives are commercially available from OSi Specialties, Endicott, N.Y.

Example 2
Comparison of Foam Dissipation and Spray Aesthetics for Compositions Using Various Additives The contact foam dissipation and spray aesthetics of the compositions of example 1 are tested by the following methods.

Contact Foam Dissipation

A 4.0 second burst is sprayed at a forty-five degree angle, 1 inch from the benchtop. Timing begins immediately after spraying and stops when the foam is completely dissipated.

Spray Aesthetics

The sprays are subjectively rated as follows:

A=sprays have fine uniform particles of approximately 40 $\mu$m is size;

B=sprays have uniform particles with some minor amount of a larger particle size;

C=sprays have a large proportion of unevenly sized particles, resulting in spitting spray; and D=sprays are narrow, possibly single stream sprays.

The results are shown in Table I below.

TABLE I

| Additive | Foam Dissipation | Spray Aesthetics |
|---|---|---|
| Control (w/o additive) | 3 | C- |
| Silwet L-722 | 5 | A |
| Silwet L-720 | 13 | C- |
| Silwet L-7001 | 15 | C- |
| Silwet 7002 | 15 | C- |
| Silwet L-7200 | 17 | C- |
| Silwet L-7500 | 4 | A |
| Silwet L-7600 | 8 | C- |
| Silwet L-7604 | 19 | C- |
| Silwet L-7605 | 15 | C- |
| Silwet L-7622 | 16 | C- |
| DC-344 | 10 | A- |
| Silwet L-7602 | 16 | C |
| Silwet L-7087 | 13 | B+ |
| Silwet L-7657 | 18 | C- |
| Silsoft 900 | 3 | A |

As can be seen from Table I, only three additives at the 0.3% level tested positively for improving both spray aesthetics and for reducing contact foaming in a 55% VOC system, Silwet 722, Silwet L-7500 and Silsoft 900. These are the only three additives which are solely polypropylene oxide-modified polydimethylsiloxane block copolymers (contain no polyethylene oxide-modified polydimethylsiloxane block copolymers).

Example 3
Effect of Various Additive Levels

Example 2 is repeated using samples prepared with varying levels of the additive Silwet L-722. The results are shown in Table II below.

TABLE II

| % Amount of Additive Silwet L-722 | Foam Dissipation | Spray Aesthetics |
|---|---|---|
| 0.3 | 5 | A |
| 0.2 | 7 | A |
| 0.1 | 6 | B- |
| 0.05 | 6 | C+ |
| 0.025 | 6 | C- |
| 0.01 | 5 | C- |

As can be seen from Table II, as the level of Silwet L-722 decreases, foam dissipation is maintained, but spray aesthetics deteriorate.

Example 4
Effect of Various Additive Levels

Example 2 is repeated using samples prepared with varying levels of the additive Silwet L-7500. The results are shown in Table III below.

TABLE III

| % Amount of Additive Silwet L-7500 | Foam Dissipation | Spray Aesthetics |
|---|---|---|
| 0.3 | 4 | A |
| 0.2 | 5 | A |
| 0.1 | 5 | A |
| 0.05 | 6 | A |
| 0.025 | 7 | A |
| 0.01 | 8 | A |

As can be seen from Table III, as the level of Silwet L-7500 decreases, foam dissipation remains good though it increases slightly and spray aesthetics remain excellent.

Example 5
Effect of Various Additive Levels

Example 2 is repeated using samples prepared with varying levels of the additive Silsoft 900. The results are shown in Table IV below.

TABLE IV

| % Amount of Additive Silsoft 900 | Foam Dissipation | Spray Aesthetics |
|---|---|---|
| 0.3 | 3 | A |
| 0.2 | 3 | A |
| 0.1 | 3 | A |
| 0.05 | 3 | A- |
| 0.025 | 4 | B+ |
| 0.01 | 5 | B+ |

As can be seen from Table IV, as the level of Silsoft 900 increases, foam dissipation remains very good though it increases slightly and spray aesthetics remain excellent though they deteriorate slightly.

Example 6
Malvern Laser Light Scattering of Various Formulations

The particle size of the spray are determined using a Malvern Series 2600 Droplet and Particle Size Distribution Analyzer. The results of the tests are shown in Table V below.

TABLE V

| Additive | Level (%) | Median Size ($\mu$m) | Mean Size ($\mu$m) |
|---|---|---|---|
| Control (w/o additive) | — | 55.99 | 73.90 |
| Silwet L-722 | 0.30 | 37.66 | 41.30 |
| Silwet L-722 | 0.20 | 44.68 | 45.51 |
| Silwet L-722 | 0.10 | 53.75 | 57.62 |
| Silwet L-722 | 0.050 | 52.34 | 64.19 |
| Silwet L-722 | 0.025 | 52.88 | 63.40 |
| Silwet L-722 | 0.010 | 51.49 | 68.16 |
| Silwet L-7500 | 0.30 | 34.88 | 37.53 |
| Silwet L-7500 | 0.20 | 36.21 | 38.89 |
| Silwet L-7500 | 0.10 | 38.05 | 40.80 |
| Silwet L-7500 | 0.050 | 40.69 | 42.14 |
| Silwet L-7500 | 0.025 | 42.02 | 47.71 |
| Silwet L-7500 | 0.010 | 54.78 | 61.13 |
| Silsoft 900 | 0.30 | 32.65 | 35.49 |
| Silsoft 900 | 0.20 | 35.11 | 37.64 |
| Silsoft 900 | 0.10 | 37.57 | 38.53 |
| Silsoft 900 | 0.050 | 36.22 | 37.87 |
| Silsoft 900 | 0.025 | 43.04 | 43.65 |
| Silsoft 900 | 0.010 | 45.03 | 46.52 |

As can be seen from Table V, the particle size of the spray correlates to the spray aesthetics with the smaller particle size achieving better spray aesthetics.

We claim:

1. A hair cosmetic composition providing improved spray aesthetics and foam dissipation comprising:

from about 0.001 to about 0.9% by weight of a polymer, said polymer being an Si—C linked polypropylene oxide-modified polydimethylsiloxane block copolymer of the alkoxy-end blocked type or the alkyl-pendant type which contains essentially no ethylene oxide;

from about 1 to about 15% by weight of at least one film-forming resin;

up to about 70% by weight of a solvent;

from about 10 to about 60% by weight of a propellant; and water as the balance;

wherein the composition contains essentially no starch syrup and no more than about 80% of one or more volatile organic compounds.

2. The composition of claim 1, wherein said composition contains no starch syrup.

3. The composition of claim 1, wherein the resin is selected from the group consisting of a copolymer of methylmethacrylate, butyl acrylate, and methacrylic acid and a copolymer of n-tert-octylacrylamide, methyl and/or ethyl methacrylate, hydroxypropyl methacrylate, acrylic acid and t-butyl aminoethyl methacrylate.

4. The composition of claim 1, wherein the additive is water insoluble.

5. The composition of claim 1, wherein the additive is hydrolytically stable.

6. The composition of claim 1, wherein said additive is an Si—C linked polypropylene oxide-modified polydimethylsiloxane block copolymer.

7. The composition of claim 1, wherein the solvent is a lower alcohol.

8. A hair cosmetic composition providing improved spray aesthetics and foam dissipation consisting essentially of:

from about 0.001 to about 0.9% by weight of a polymer, said polymer being an Si—C linked polypropylene oxide-modified polydimethylsiloxane block copolymer of the alkoxy-end blocked type or the alkyl-pendant type which contains essentially no ethylene oxide;

from about 1 to about 15% by weight of at least one film-forming resin;

up to about 70% by weight of a solvent;

from about 10 to about 60% by weight of a propellant; and water as the balance, wherein the composition contains no more than about 80% of one or more volatile organic compounds.

9. The composition of claim 8, wherein the resin is selected from the group consisting of a copolymer of methylmethacrylate, butyl acrylate, and methacrylic acid and a copolymer of n-tert-octylacrylamide, methyl and/or ethyl methacrylate, hydroxypropyl methacrylate, acrylic acid and t-butyl aminoethyl methacrylate.

10. The composition of claim 8, wherein the additive is water insoluble.

11. The composition of claim 8, wherein the additive is hydrolytically stable.

12. The composition of claim 8, wherein said additive is an Si—C linked polypropylene oxide-modified polydimethylsiloxane block copolymer.

13. A method for improving the spray aesthetics and foam dissipation of a hair cosmetic composition which contains no more than about 80% of one or more volatile organic compounds comprising from about 1 to about 15% by weight of a film-forming resin; up to about 70% by weight of a solvent; from about 10 to about 60% by weight of a propellant; and water as the balance, the method comprising formulating the composition with from about 0.001 to about 0.9% by weight of a polymer, said polymer being an Si—C linked polypropylene oxide-modified polydimethylsiloxane block copolymer of the alkoxy-end blocked type or the alkyl-pendant type which contains essentially no ethylene oxide.

14. The composition of claim 13, wherein the resin is selected from the group consisting of a copolymer of methylmethacrylate, butyl acrylate, and methacrylic acid and a copolymer of n-tert-octylacrylamide, methyl and/or ethyl methacrylate, hydroxypropyl methacrylate, acrylic acid and t-butyl aminoethyl methacrylatemethylmethacrylate, butyl acrylate, and methacrylic acid.

15. The composition of claim 13, wherein the additive is water insoluble.

16. The composition of claim 13, wherein the additive is hydrolytically stable.

17. The composition of claim 13, wherein said additive is an Si—C linked polypropylene oxide-modified polydimethylsiloxane block copolymer.

* * * * *